United States Patent
Lautenbach et al.

(10) Patent No.: US 8,052,996 B2
(45) Date of Patent: *Nov. 8, 2011

(54) TWO-PIECE, INTERNAL-CHANNEL OSMOTIC DELIVERY SYSTEM FLOW MODULATOR

(75) Inventors: Scott D. Lautenbach, San Mateo, CA (US); Pedro E. de la Serna, San Jose, CA (US); Pauline C. Zamora, Sausalito, CA (US); Michael A. DesJardin, Sunnyvale, CA (US)

(73) Assignee: Intarcia Therapeutics, Inc., Hayward, CA (US)

(*) Notice: Subject to any disclaimer, the term of this patent is extended or adjusted under 35 U.S.C. 154(b) by 1103 days.

This patent is subject to a terminal disclaimer.

(21) Appl. No.: 11/755,494

(22) Filed: May 30, 2007

(65) Prior Publication Data

US 2007/0281024 A1    Dec. 6, 2007

Related U.S. Application Data

(63) Continuation-in-part of application No. 11/347,562, filed on Feb. 3, 2006.

(60) Provisional application No. 60/809,451, filed on May 30, 2006, provisional application No. 60/650,225, filed on Feb. 3, 2005.

(51) Int. Cl.
  *A61K 9/24* (2006.01)
  *A61K 9/22* (2006.01)
  *A61F 2/00* (2006.01)

(52) U.S. Cl. .................. 424/473; 604/892.1; 424/423

(58) Field of Classification Search .................. 424/473; 604/892.1, 222
See application file for complete search history.

(56) References Cited

U.S. PATENT DOCUMENTS

| | | | |
|---|---|---|---|
| 4,655,462 A | 4/1987 | Balsells |
| 4,826,144 A | 5/1989 | Balsells |
| 4,830,344 A | 5/1989 | Balsells |
| 4,876,781 A | 10/1989 | Balsells |
| 4,893,795 A | 1/1990 | Balsells |
| 4,907,788 A | 3/1990 | Balsells |
| 4,915,366 A | 4/1990 | Balsells |
| 4,934,666 A | 6/1990 | Balsells |
| 4,961,253 A | 10/1990 | Balsells |
| 4,964,204 A | 10/1990 | Balsells |

(Continued)

FOREIGN PATENT DOCUMENTS

EP    1600187    11/2005

(Continued)

OTHER PUBLICATIONS

Written Opinion of the International Searching Authority, Re: PCT/US2007/069990, Date of Mailing of Search Report: Feb. 26, 2008.

(Continued)

*Primary Examiner* — Blessing Fubara
(74) *Attorney, Agent, or Firm* — Gary R. Fabian; Barbara G. McClung

(57) ABSTRACT

An osmotic delivery system flow modulator includes an outer shell constructed and arranged for positioning in an opening, an inner core inserted in the outer shell, and a fluid channel having a spiral shape defined between the outer shell and the inner core. The fluid channel is adapted for delivery of an active agent formulation from the reservoir of the osmotic delivery system.

17 Claims, 5 Drawing Sheets

U.S. PATENT DOCUMENTS

| | | |
|---|---|---|
| 4,974,821 A | 12/1990 | Balsells |
| 5,072,070 A | 12/1991 | Balsells |
| 5,079,388 A | 1/1992 | Balsells |
| 5,108,078 A | 4/1992 | Balsells |
| 5,117,066 A | 5/1992 | Balsells |
| 5,134,244 A | 7/1992 | Balsells |
| 5,160,122 A | 11/1992 | Balsells |
| 5,161,806 A | 11/1992 | Balsells |
| 5,203,849 A | 4/1993 | Balsells |
| 5,413,572 A | 5/1995 | Wong et al. |
| 5,728,396 A | 3/1998 | Peery et al. |
| 5,904,935 A | 5/1999 | Eckenhoff et al. |
| 5,932,547 A | 8/1999 | Stevenson et al. |
| 5,972,370 A | 10/1999 | Eckenhoff et al. |
| 5,985,305 A | 11/1999 | Peery et al. |
| 5,997,527 A | 12/1999 | Gumucio et al. |
| 6,113,938 A | 9/2000 | Chen et al. |
| 6,124,261 A | 9/2000 | Stevenson et al. |
| 6,132,420 A | 10/2000 | Dionne et al. |
| 6,156,331 A | 12/2000 | Peery et al. |
| 6,217,906 B1 | 4/2001 | Gumucio et al. |
| 6,235,712 B1 | 5/2001 | Stevenson et al. |
| 6,261,584 B1 | 7/2001 | Peery et al. |
| 6,270,787 B1 | 8/2001 | Ayer |
| 6,287,295 B1 | 9/2001 | Chen et al. |
| 6,375,978 B1 | 4/2002 | Kleiner et al. |
| 6,395,292 B2 | 5/2002 | Peery et al. |
| 6,508,808 B1 | 1/2003 | Carr et al. |
| 6,524,305 B1 * | 2/2003 | Peterson et al. ........... 604/892.1 |
| 6,544,252 B1 | 4/2003 | Theeuwes et al. |
| 6,635,268 B2 | 10/2003 | Peery et al. |
| 6,682,522 B2 | 1/2004 | Carr et al. |
| 6,840,931 B2 | 1/2005 | Peterson et al. |
| 6,923,800 B2 | 8/2005 | Chen et al. |
| 6,939,556 B2 | 9/2005 | Lautenbach |
| 6,976,981 B2 | 12/2005 | Ayer |
| 6,997,922 B2 | 2/2006 | Theeuwes et al. |
| 7,014,636 B2 | 3/2006 | Gilbert |
| 7,074,423 B2 | 7/2006 | Fereira et al. |
| 7,112,335 B2 | 9/2006 | Lautenbach |
| 7,163,688 B2 | 1/2007 | Peery et al. |
| 7,207,982 B2 | 4/2007 | Dionne et al. |
| 7,258,869 B1 | 8/2007 | Berry et al. |
| 7,682,356 B2 | 3/2010 | Alessi et al. |
| 7,879,028 B2 | 2/2011 | Alessi et al. |
| 2004/0039376 A1 * | 2/2004 | Peery et al. ................. 604/890.1 |
| 2004/0102762 A1 * | 5/2004 | Gilbert ........................ 604/892.1 |
| 2004/0224903 A1 | 11/2004 | Berry et al. |
| 2004/0265273 A1 * | 12/2004 | Li et al. ......................... 424/93.2 |
| 2005/0008661 A1 | 1/2005 | Fereira et al. |
| 2005/0112188 A1 | 5/2005 | Eliaz et al. |
| 2005/0175701 A1 | 8/2005 | Pan et al. |
| 2005/0266087 A1 | 12/2005 | Junnarkar et al. |
| 2005/0276856 A1 | 12/2005 | Fereira et al. |
| 2006/0193918 A1 | 8/2006 | Rohloff et al. |
| 2006/0216242 A1 | 9/2006 | Rohloff et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2007/0281024 A1 | 12/2007 | Lautenbach et al. |
| 2011/0166554 A1 | 7/2011 | Alessi et al. |

FOREIGN PATENT DOCUMENTS

WO    WO 02/085428    10/2002

OTHER PUBLICATIONS

International Search Report of International Searching Authority, Re: PCT/US2007/069990, Date of Mailing of Search Report: Feb. 26, 2008.

* cited by examiner

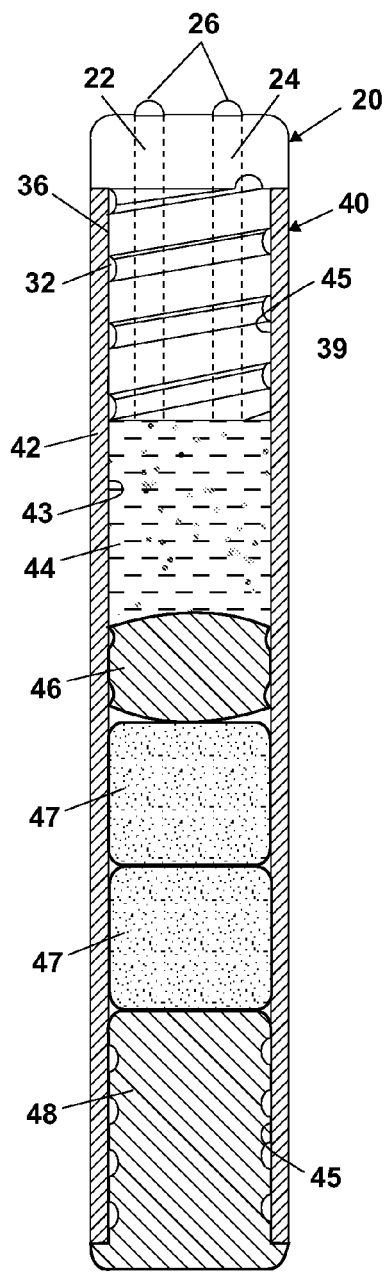
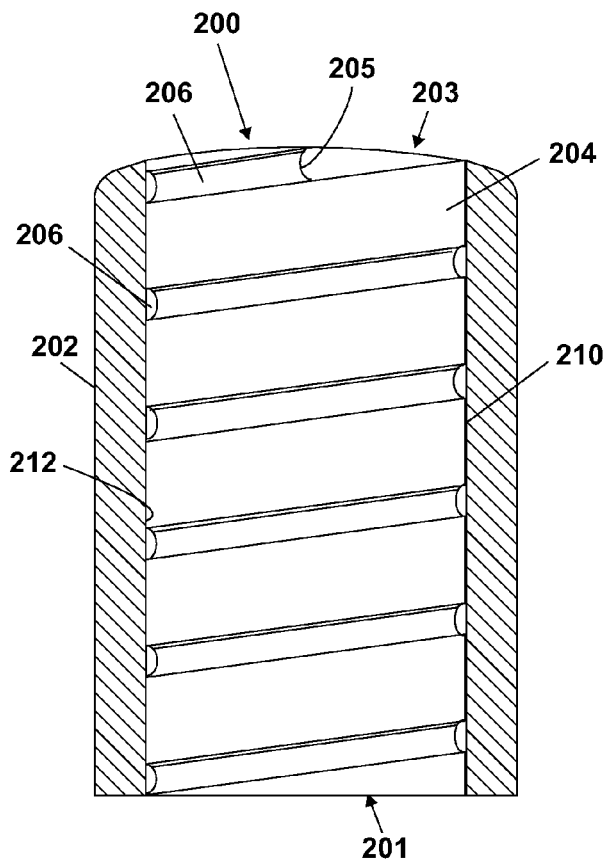
*(PRIOR ART)*
FIG. 1
FIG. 2A

TWO-PIECE, INTERNAL-CHANNEL OSMOTIC DELIVERY SYSTEM FLOW MODULATOR

CROSS-REFERENCE TO RELATED APPLICATIONS

This application claims the benefit of U.S. Provisional Application Ser. No. 60/809,451, filed 30 May 2006, which application is herein incorporated by reference in its entirety; and is a continuation-in-part of U.S. patent application Ser. No. 11/347,562, filed 3 Feb. 2006, which claims the benefit of U.S. Provisional Application Ser. No. 60/650,225, filed 3 Feb. 2005.

BACKGROUND OF THE INVENTION

The invention relates generally to osmotic delivery systems for sustained delivery of active agents in fluid environments. More particularly, the invention relates to a flow modulator for delivering an active agent from an osmotic delivery system in a fluid environment.

FIG. 1 illustrates a prior-art osmotic delivery system 40, as described in U.S. Pat. No. 6,524,305 issued to Peterson et al. The osmotic delivery system 40 includes an enclosure 42 containing osmotic agent 47 and active agent 44. A dividing member 46 forms a partition between the osmotic agent 47 and the active agent 44. A semipermeable plug 48 is inserted into a first opening 45 of the enclosure 42. The semipermeable plug 48 selectively permits fluid to enter the interior of the enclosure 42. A flow modulator 20 is inserted into a second opening 39 of the enclosure 42. The flow modulator 20 allows the active agent 44 to exit the interior of the enclosure 42 while controlling back-diffusion of fluids into the interior of the enclosure 42. When the osmotic delivery system 40 is disposed in a fluid environment, fluid from the exterior of the enclosure 42 enters the enclosure 42 through the semipermeable plug 48 and permeates the osmotic agent 47, causing the osmotic agent 47 to swell. The osmotic agent 47 displaces the dividing member 46 as it swells, causing an amount of the active agent 44 to be delivered to the environment of use through the flow modulator 20.

In the prior-art osmotic delivery system 40 shown in FIG. 1, the outer surface of the flow modulator 20 includes a helical delivery path 32 through which the active agent 44 passes from the interior to the exterior of the enclosure 42. The thread 36 which defines the helical delivery path 32 abuts the interior surface 43 of the enclosure 42 so that the active agent 44 comes into contact with the interior surface 43 of the enclosure 42 as it passes through the helical delivery path 32. The pitch, amplitude, cross-sectional area, and shape of the helical delivery path 32 are selected such that back-diffusion into the enclosure 42 from the fluid environment is minimized. Fill hole 22 and vent hole 24 are provided in the flow modulator 20. When assembling the osmotic delivery system 40, the flow modulator 20 is first inserted in the enclosure 42. The active agent 44 is then injected into the enclosure 42 through the fill hole 22, while gases in the enclosure 42 escape through the vent hole 24. Thereafter, caps 26 are inserted in the holes 22, 24 so that delivery of the active agent 44 occurs only through the helical delivery path 32.

From the foregoing, there continues to be a desire to provide additional reliability and flow modulator capabilities in osmotic delivery systems.

SUMMARY OF THE INVENTION

In one aspect, the invention relates to an osmotic delivery system flow modulator which comprises an outer shell constructed and arranged for positioning in an opening of a reservoir of an osmotic delivery system, an inner core inserted in the outer shell, and a fluid channel having a spiral shape defined between the outer shell and the inner core, the fluid channel being adapted for delivery of an active agent formulation from the reservoir of the osmotic delivery system.

In another aspect, the invention relates to an osmotic delivery system which comprises a reservoir, a semipermeable plug disposed at a first end of the reservoir to selectively permit flow into the reservoir, a flow modulator disposed at a second end of the reservoir, the flow modulator comprising an internal spiral channel adapted for delivery of an active agent formulation contained in the reservoir to a fluid environment in which the osmotic delivery system operates.

In yet another aspect, the invention relates to an implantable delivery system for an active agent formulation which comprises a reservoir made of an impermeable material, a first chamber in the reservoir containing an osmotic engine, a second chamber in the reservoir containing an active agent formulation, a semipermeable plug disposed at a first end of the reservoir adjacent the first chamber, and a flow modulator as described above disposed at a second end of the reservoir adjacent the second chamber.

Other features and advantages of the invention will be apparent from the following description and the appended claims.

BRIEF DESCRIPTION OF THE DRAWINGS

The accompanying drawings, described below, illustrate typical embodiments of the invention and are not to be considered limiting of the scope of the invention, for the invention may admit to other equally effective embodiments. The figures are not necessarily to scale, and certain features and certain view of the figures may be shown exaggerated in scale or in schematic in the interest of clarity and conciseness.

FIG. 1 depicts a cross-sectional view of a prior-art osmotic delivery system.

FIG. 2A depicts a partial cross-sectional view of a flow modulator having an inner core inserted in an outer shell and an internal spiral fluid channel formed in the inner core.

DETAILED DESCRIPTION OF THE INVENTION

Figure 2C:
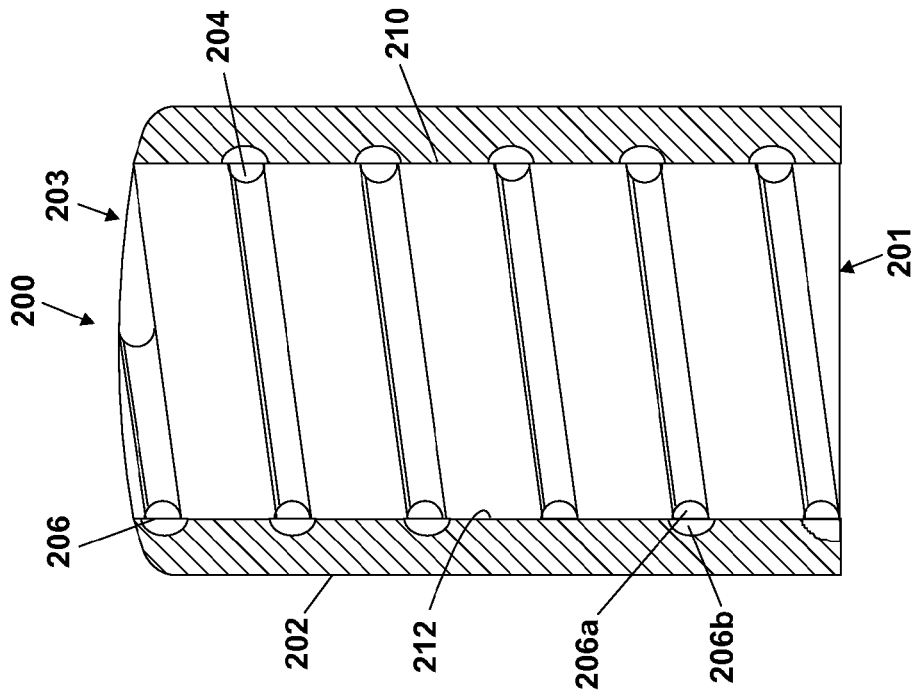
FIG. 2C depicts a partial cross-sectional view of a flow modulator having an inner core inserted in an outer shell and an internal spiral fluid channel formed in the inner core and the outer shell.

The invention will now be described in detail with reference to a few preferred embodiments, as illustrated in the accompanying drawings. In describing the preferred embodiments, numerous specific details are set forth in order to provide a thorough understanding of the invention. However, it will be apparent to one skilled in the art that the invention may be practiced without some or all of these specific details. In other instances, well-known features and/or process steps have not been described in detail so as not to unnecessarily obscure the invention. In addition, like or identical reference numerals are used to identify common or similar elements.

FIGS. 2A through 2E depict partial cross-sectional views of a flow modulator 200 for delivery of an active agent formulation from a reservoir of an osmotic delivery system. Referring to FIG. 2A, the flow modulator 200 has an inlet side 201, which is the side that would be exposed to the active agent formulation in the reservoir of the osmotic delivery system, and an outlet side 203, which is the side that would be exposed to a fluid environment in which the osmotic delivery system operates. Typically, the fluid environment is an aqueous environment, that is, the fluid environment contains water. The flow modulator 200 includes an outer shell 202 and a generally cylindrical inner core 204 inserted in the outer shell 202. Extending from the inlet side 201 to the outlet side 203 of the flow modulator 200, between the outer shell 202 and the inner core 204, is a fluid channel 206 having a spiral shape. All or a substantial portion of the fluid channel 206 may have a spiral shape. The fluid channel 206 is internal to the flow modulator 200. The flow modulator 200 therefore forms a barrier between active agent formulation passing through the fluid channel 206 and the reservoir of the osmotic delivery system.

Figure 2B:
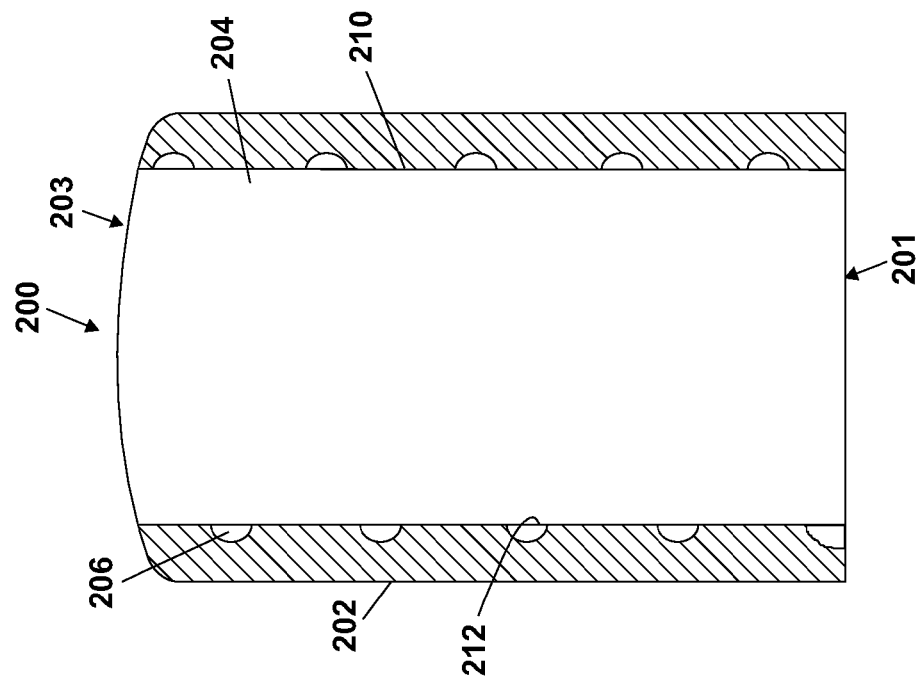
FIG. 2B depicts a partial cross-sectional view of a flow modulator having an inner core inserted in an outer shell and an internal spiral fluid channel formed in the outer shell.
Figure 2E:
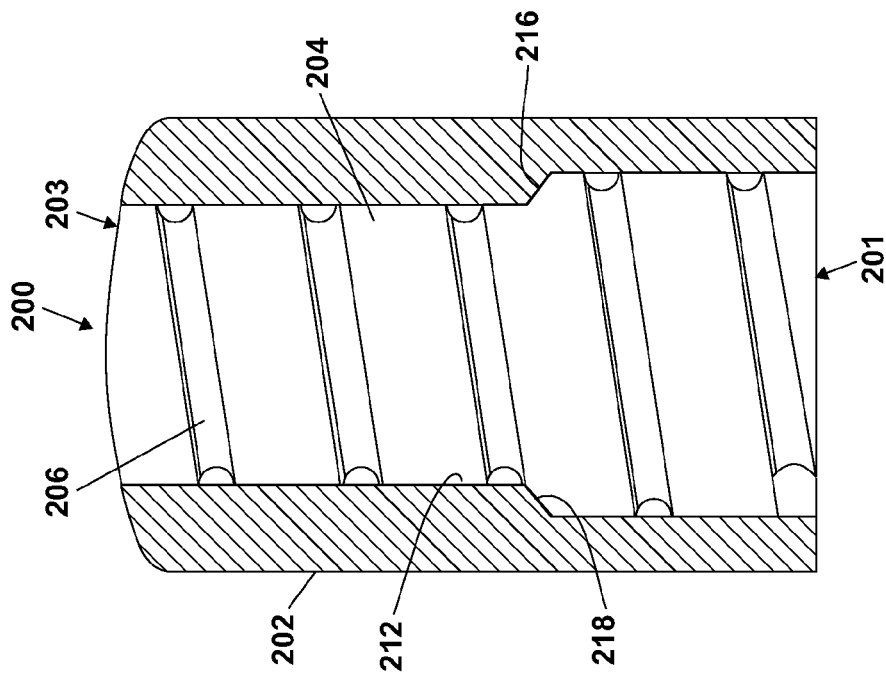
FIG. 2E depicts a partial cross-section view of a flow modulator having an inner core inserted in an outer shell and mating surfaces on the inner core and outer shell for preventing expulsion of the inner core from the outer shell.
Figure 2D:
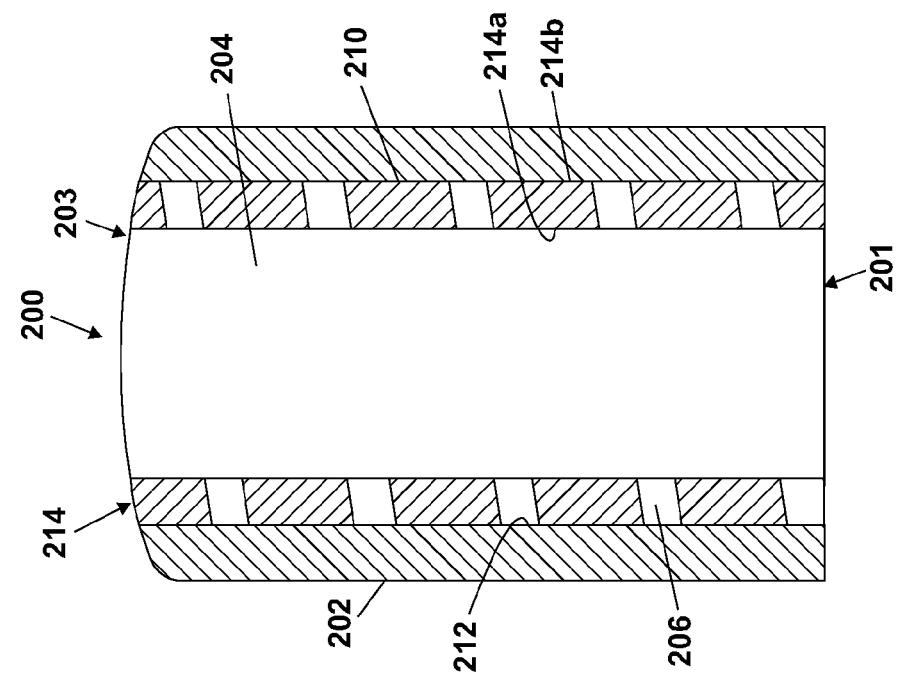
FIG. 2D depicts a partial cross-sectional view of a flow modulator having an inner core inserted in an outer shell and a flow insert including an internal spiral fluid channel interposed between the inner core and the outer shell.

In FIGS. 2A-2C, the outer surface 210 of the inner core 204 mates with the inner surface 212 of the outer shell 202. The fluid channel 206 may be formed in the outer surface 210 of the inner core 204, as shown in FIG. 2A, or in the inner surface 212 of the outer shell 202, as shown in FIG. 2B. Alternatively, as shown in FIG. 2C, the fluid channel 206 may include a first fluid channel 206a formed in the outer surface 210 of the inner core 204 and a second fluid channel 206b formed in the inner surface 212 of the outer shell 202, wherein the first fluid channel 206a and the second fluid channel 206b are adjacent to each other or in communication. All or a substantial portion of each of the fluid channels 206a, 206b has a spiral shape. Alternatively, as shown in FIG. 2D, a flow insert 214 may be disposed between the outer surface 210 of the inner core 204 and the inner surface 212 of the outer shell 202, wherein the flow insert 214 provides the fluid channel 206. The flow insert 214 may be a coiled tube, for example, wherein the spaces between the coils of the tube serve as the fluid channel 206. Alternatively, the flow insert 214 may be a hollow cylindrical body or a sleeve in which a spiral groove is formed, where the spiral groove serves as the fluid channel 206. The fluid channel 206 may have any desired cross-section, examples of which include circular or D shape. D-shaped fluid channels are shown in FIGS. 2A-2E. The length of the fluid channel 206 depends on the configuration of the osmotic delivery system and the desired release rate. Typically, the (spiral) length of the fluid channel 206 ranges from 10 to 50 mm. Typically, the effective cross-sectional diameter of the fluid channel 206 ranges from 0.1 to 0.5 mm. These ranges are given as examples and are not intended to limit the invention as otherwise described herein.

Referring to FIGS. 2A-2D, the largest outer diameter of the inner core 204 and the largest inner diameter of the outer shell 202 are selected such that there is an interference fit or a seal between the outer surface 210 of the inner core 204 and the inner surface 212 of the outer shell 202. This interference fit or seal confines the flow of formulation to the fluid channel 206. This interference fit or seal may be sufficient to prevent expulsion of the inner core 204 and/or flow insert 214 from the outer shell 202. On the other hand, in FIGS. 2A-2C, the mating portion of the surfaces 210, 212 of the inner core 204 and outer shell 202, respectively, may include features such as threaded connection, bonded connection, welded connection, and the like to additionally secure the inner core 204 to the outer shell 202. In FIG. 2D, similar connection features may be formed between the portions of the inner and outer surfaces 214a, 214b of the flow insert 214 which mate with the surfaces 210, 212 of the inner core 204 and outer shell 202, respectively. FIG. 2E discloses an alternate method for preventing expulsion of the inner core 204 from the outer shell 202 which includes an outer shoulder 216 on the outer surface 210 of the inner core 204 abutting/engaging an inner shoulder 218 on the inner surface 212 of the outer shell 202. This prevents expulsion of the inner core 204 through the outlet side 203 of the flow modulator 200. The abutting/engaging surfaces of the shoulders 216, 218 may be flat or may be tapered, as shown in FIG. 2E.

The use of abutting/engaging shoulders 216, 218 to prevent expulsion of the inner core 204 from the outer shell 202 into the fluid environment in which the osmotic delivery system operates may be applied to any of the examples shown in FIGS. 2A-2D. Further, any of the features of the examples shown in FIGS. 2A-2E may be interchanged and combined to make alternate examples of the flow modulator 200. For example, in FIG. 2E, a channel having a spiral shape may also be located in the inner surface 212 of the outer shell 202, as described in FIG. 2C. Or, in FIG. 2D, channels having a spiral shape may also be located in the inner surface 212 of the outer shell 202 and/or outer surface 210 of the inner core 204, as described in FIGS. 2A and 2B, respectively, where the channels in the outer shell 202 and/or inner core 204 would be adjacent to or in communication with the fluid channel 206 in the flow insert 214.

Referring to FIGS. 2A-2E, the outer shell 202, the inner core 204, and the flow insert 214 are preferably formed from a material that is inert and biocompatible. Examples of inert, biocompatible materials include, but are not limited to, non-reactive polymers and metals such as titanium, stainless steel, platinum and their alloys, and cobalt-chromium alloys. Non-reactive polymers are useful where it is desirable to avoid interaction between the active agent formulation and a metallic material as the active agent formulation is delivered to the fluid environment in which the osmotic delivery system operates. Examples of suitable non-reactive polymers include, but are not limited to, polyaryletherketones, such as polyetheretherketone and polyaryletheretherketone, ultra-high molecular weight polyethylene, fluorinated ethylene-propylene, polymethylpentene, and liquid crystal polymers. Preferably, at least the surfaces of the outer shell 202, the inner core 204, and the flow insert 214 which would be exposed to the active agent formulation as the active agent formulation flows through the fluid channel 206 are made of or coated with a material that would not have a detrimental effect on the active agent formulation. In a preferred example, the aforementioned surfaces are made of a non-metallic material that is inert and biocompatible. Such non-metallic material could be a non-reactive polymer, examples of which are given above.

The length, the cross-sectional shape, and flow area of the fluid channel 206 may be selected such that the average linear velocity of the active agent formulation through the fluid channel 206 is higher than that of the linear inward influx of materials due to diffusion or osmosis from the fluid environment in which the osmotic delivery system operates. This would have the effect of attenuating or moderating back diffusion, which if not controlled could contaminate the active agent formulation in the osmotic delivery system. The release rate of the active agent formulation can be modified by modifying the geometry of the fluid channel 206, as described below.

The convective flow of an active agent through the fluid channel 206 is determined by the pumping rate of the osmotic delivery system and the concentration of the active agent in the active agent formulation in the reservoir of the osmotic delivery system. The convective flow may be expressed as follows:

$$Q_{ca} = (Q)(C_a) \quad (1)$$

where $Q_{ca}$ is the convective transport of beneficial in mg/day, Q is the overall convective transport of the active agent formulation in cm$^3$/day, and $C_a$ is the concentration of active agent in the active agent formulation within the reservoir of the osmotic delivery system in mg/cm$^3$.

The diffusive flow of active agent out of the fluid channel 206 is a function of active agent concentration and diffusivity and cross-sectional shape and length of the fluid channel 206. The diffusive flow may be expressed as follows:

$$Q_{da} = \frac{D\pi r^2 \Delta C_a}{L} \quad (2)$$

where $Q_{da}$ is the diffusive transport of the active agent in mg/day, D is the diffusivity through the fluid channel 206 in cm$^2$/day, r is the effective inner radius of the fluid channel 206 in cm, $\Delta C_a$ is the difference between the concentration of the active agent in the active agent formulation in the reservoir of the osmotic delivery system and the concentration of the active agent in the fluid environment outside of the delivery orifice 205 of the flow modulator 200 in mg/cm$^3$, and L is the (spiral) length of the fluid channel 206 in cm.

In general, the concentration of active agent in the active agent formulation in the osmotic delivery system is much greater than the concentration of the active agent in the fluid environment of use such that the difference, $\Delta C_a$ can be approximated by the concentration of the active agent within the active agent formulation in the osmotic delivery system, $C_a$. Thus:

$$Q_{da} = \frac{D\pi r^2 C_a}{L} \quad (3)$$

It is generally desirable to keep diffusive flux of the active agent much less than convective flow of the active agent. This is represented as follows:

$$\frac{Q_{da}}{Q_{ca}} = \frac{D\pi r^2 C_a}{QC_a L} = \frac{D\pi r^2}{QL} < 1 \quad (4)$$

Equation (4) indicates that the relative diffusive flux decreases with increasing volumetric flow rate and path length, increases with increasing diffusivity and channel radius, and is independent of active agent concentration.

The diffusive flux of water where the fluid channel 206 opens into the osmotic delivery system can be approximated as follows:

$$Q_{wd}(\text{res}) = C_o Q e^{(-QL/D_w A)} \quad (5)$$

where $C_o$ is the concentration profile of water in mg/cm$^3$, Q is the mass flow rate in mg/day, L is the length of the fluid channel 206 in cm, $D_w$ is the diffusivity of water through the material in the fluid channel 206 in cm$^2$/day, and A is the cross-sectional area of the fluid channel 206 in cm.

The hydrodynamic pressure drop across the delivery orifice can be calculated as follows:

$$\Delta P = \frac{8QL\mu}{\pi r^4} \quad (6)$$

where Q is the mass flow rate in mg/day, L is the length of the spiral fluid channel in cm, $\mu$ is the viscosity of the formulation, and r is the effective inner radius of the fluid channel in cm.

Figure 3:
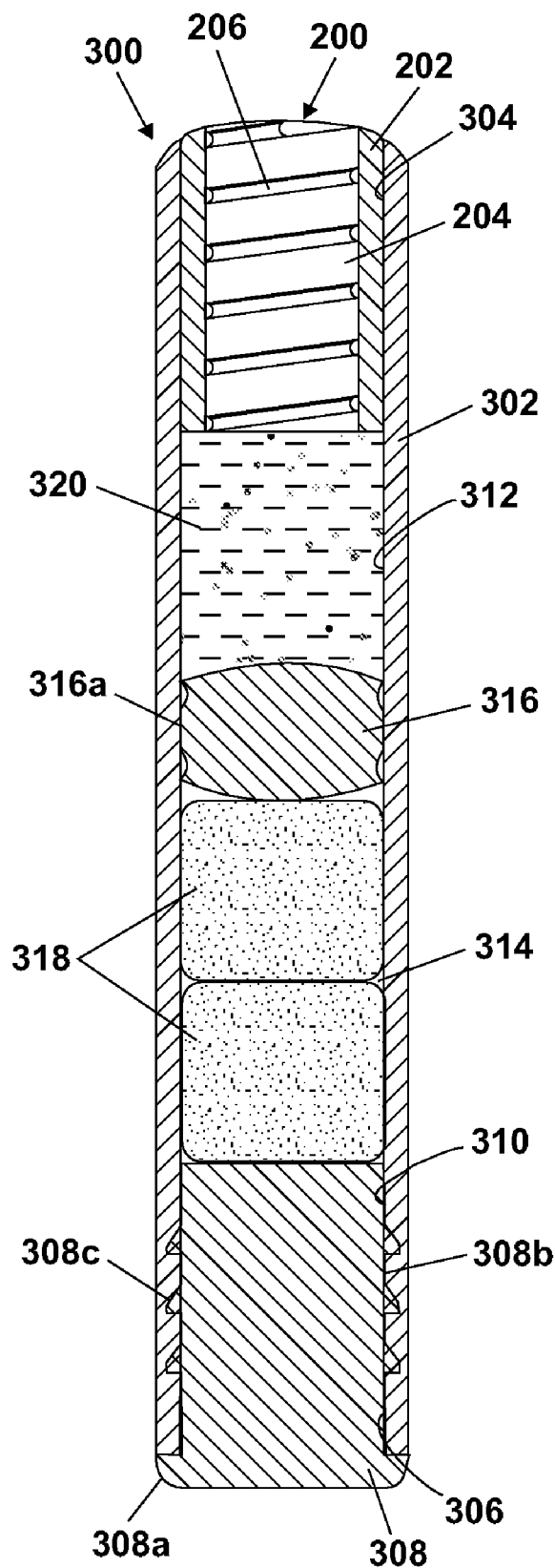
FIG. 3 depicts a cross-sectional view of an osmotic delivery system with the flow modulator of FIG. 2A.

FIG. 3 shows an osmotic delivery system 300 including the flow modulator 200. Although the osmotic delivery system 300 is shown with the flow modulator 200 of FIG. 2A, it should be clear that any of the flow modulators 200 shown in FIGS. 2A-2E may be used with the osmotic delivery system 300. The osmotic delivery system 300 includes a reservoir 302, which may be sized such that it can be implanted within a body. The reservoir 302 has open ends 304, 306. The flow modulator 200 is inserted in the open end 304. A semipermeable plug 308 is inserted in the open end 306.

The semipermeable plug 308 is a membrane that controls rate of flow of fluid from the fluid environment in which the osmotic delivery system operates into the reservoir 302. The semipermeable plug 308 allows fluid from the fluid environment to enter the reservoir 302. Compositions in the reservoir 302 are prevented from flowing out of the reservoir 302 through the semipermeable plug 308 because of the semipermeable nature of the semipermeable plug 308. The semipermeable plug 308 may be inserted partially or fully into the open end 306. In the former case, the semipermeable plug 308 may include an enlarged end portion 308a which acts as a stop member engaging an end of the reservoir 302. The outer surface 308b of the semipermeable plug 308 may have protrusions or ribs 308c that engage the inner surface 310 of the reservoir 302, thereby locking the semipermeable plug 308 to the reservoir 302 and allowing a seal to be formed between the reservoir 302 and the semipermeable plug 308. The reservoir 302 may also include undercuts which receive the protrusions 308c on the semipermeable plug 308. Semipermeable materials for the semipermeable plug 308 are those that can conform to the shape of the reservoir 302 upon wetting and that can adhere to the inner surface 310 of the reservoir 302. Typically, these materials are polymeric materials, which can be selected based on the pumping rates and system configuration requirements. Examples of suitable semipermeable materials include, but are not limited to, plasticized cellulosic materials, enhanced polymethyl methacrylates (PMMAs) such as hydroxyethylmethacrylate (HEMA), and elastomeric materials, such as polyurethanes and polyamides, polyetherpolyamind copolymers, thermoplastic copolyesters, and the like. Polyurethanes are generally preferred.

Two chambers 312, 314 are defined inside the reservoir 302. The chambers 312, 314 are separated by a partition 316, such as a slidable piston or flexible diaphragm, which is configured to fit within and make sealing contact with the reservoir 302 and to move or deform longitudinally within the reservoir 302. Preferably, the partition 316 is formed of an impermeable resilient material. As an example, the partition 316 may be a slidable piston made of an impermeable resilient material and may include annular ring shape protrusions 316a that form a seal with the inner surface 310 of the reservoir 302. Osmotic engine 318 is disposed in the chamber 314 adjacent the semipermeable plug 308, and an active agent formulation 320 is disposed in the chamber 312 adjacent the flow modulator 200. The partition 316 isolates the active agent formulation 320 from the environmental fluids that are permitted to enter the reservoir 302 through the semipermeable plug 308 such that in use, at steady-state flow, the active agent formulation 320 is expelled through the fluid channel 206 at a rate corresponding to the rate at which fluid from the fluid environment flows into reservoir 302 through the semipermeable plug 308.

The osmotic engine 318 may be in the form of tablets as shown. One or more such tablets may be used. Alternatively, the osmotic engine 318 may have other shape, texture, density, and consistency. For example, the osmotic engine 318 may be in powder or granular form. The osmotic engine 318 may include an osmopolymer. Osmopolymers are hydrophilic polymers that can imbibe aqueous fluids, such as water and biological fluids, and upon imbibing aqueous fluids swell or expand to an equilibrium state and retain a significant portion of the imbibed fluid. Osmopolymers swell or expand to a very high degree, usually exhibiting 2 to 50 fold volume increase. Osmopolymers may or may not be cross-linked. Preferred osmopolymers are hydrophilic polymers that are lightly cross-linked, such cross-links being formed by covalent or ionic bonds or residue crystalline regions after swelling. Osmopolymers can be of plant, animal or synthetic origin. Examples of osmopolymers or hydrophilic polymers suitable for use in the osmotic engine 318 include, but are not limited to, poly (hydroxy-alkyl methacrylate) having a molecular weight of from 30,000 to 5,000,000; polyvinylpyrrolidone (PVP) having a molecular weight of from 10,000 to 360,000; anionic and cationic hydrogels; polyelectrolytes complexes; polyvinyl alcohol having a low acetate residual, cross-linked with glyoxal, formaldehyde, or glutaraldehyde and having a degree of polymerization of from 200 to 30,000, a mixture of methyl cellulose, cross-linked agar and carboxymethyl cellulose; a mixture of hydroxypropyl methylcellulose and sodium carboxymethylcellulose; a mixture of hydroxypropyl ethylcellulose and sodium carboxymethyl cellulose; sodium carboxymethylcellulose; potassium carboxymethylcellulose; a water insoluble, water swellable copolymer formed from a dispersion of finely divided copolymer of maleic anhydride with styrene, ethylene, propylene, butylene or isobutylene cross-linked with from 0.001 to about 0.5 moles of saturated cross-linking agent per mole of maleic anhydride per copolymer; water swellable polymers of N-vinyl lactams; polyoxyethylene-polyoxypropylene gel; polyoxybutylene-polyethylene block copolymer gel; carob gum; polyacrylic gel; polyester gel; polyuria gel; polyether gel; polyamide gel; polycellulosic gel; polygum gel; and initially dry hydrogels that imbibe and absorb water which penetrates the glassy hydrogel and lowers its glass temperature. Other examples of osmopolymers include polymers that form hydrogels, such as CARBOPOL®, acidic carboxypolymer, a polymer of acrylic and cross-linked with a polyallyl sucrose, also known as carboxypolymethylene and carboxyvinyl polymer having a molecular weight of 250,000 to 4,000,000; CYNAMER® polyacrylamides; cross-linked water swellable indene-maleic anhydride polymers; GOODRITE® polyacrylic acid having a molecular weight of 80,000 to 200,000; POLYOX® polyethylene oxide polymer having a molecular weight of 100,000 to 5,000,000 and higher; starch graft copolymers; AQUA-KEEPS® acrylate polymer polysaccharides composed of condensed glucose units such as diester cross-linked polygluran; and the like. The osmotic engine 318 may also include an osmagent either in addition to or in lieu of the osmopolymer. Osmagents include inorganic and organic compounds that exhibit an osmotic pressure gradient across a semipermeable wall against an external fluid. Osmagents imbibe fluid into the osmotic system, thereby making available fluid to push against the formulation for delivery through the flow modulator. Osmagents are also known as osmotically effective compounds or solutes. Osmagents useful in the osmotic engine 318 include magnesium sulfate, magnesium chloride, sodium chloride, potassium sulfate, sodium sulfate, lithium sulfate, potassium acid phosphate, mannitol, urea, inositol, magnesium succinate, tartaric acid, carbohydrates such as raffinose, sucrose, glucose, lactose, sorbitol, and mixtures thereof.

The active agent formulation 320 may include one or more active agents. The active agent may be any physiologically or pharmacologically active substance, particularly those known to be delivered to the body of a human or an animal, such as medicaments, vitamins, nutrients, or the like. Active agents which may be delivered by the osmotic delivery system 300 through the flow modulator 200 include, but are not limited to, drugs that act on infectious diseases, chronic pain, diabetes, the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species. Preferred active agents include macromolecules (proteins and peptides) and active agents that are highly potent. The active agent can be present in a wide variety of chemical and physical forms, such as solids, liquids and slurries. In addition to the one or more active agents, the formulation 320 may optionally include pharmaceutically acceptable carriers and/or additional ingredients such as antioxidants, stabilizing agents, buffers, and permeation enhancers.

Materials that are used for the reservoir 302 should be sufficiently rigid to withstand expansion of the osmotic engine 318 without changing its size or shape. Further, the materials should ensure that the reservoir 302 will not leak, crack, break, or distort under stress to which it could be subjected during implantation or under stresses due to the pressures generated during operation. The reservoir 302 may be formed of inert, biocompatible, natural or synthetic materials which are known in the art. The material of the reservoir 302 may or may not be bioerodible. A material that is bioerodible will at least in part dissolve, degrade, or otherwise erode in the fluid environment of use. Preferably, the material of the reservoir 302 is non-bioerodible. Generally, preferred materials for the reservoir 302 are those acceptable for human implantation. Preferably, the material of the reservoir 302 is impermeable, particularly when stability of the formulation in the reservoir 302 is sensitive to the fluid environment of use. Examples of materials suitable for the reservoir 302 include non-reactive polymers or biocompatible metals or alloys. Examples of non-reactive polymers for the reservoir 302 include, but are not limited to, acrylonitrile polymers such as acrylonitrile-butadiene-styrene terpolymer; halogenated polymers such as polytetraflouroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; and polystyrene. Examples of metallic materials for the reservoir 302 include, but are not limited to, stainless steel, titanium, platinum, tantalum, gold, and their alloys, as well as gold-plated ferrous alloys, platinum-plated ferrous alloys, cobalt-chromium alloys and titanium nitride coated stainless steel. For size-critical applications, high payload capability, long duration applications, and applications where the formulation is sensitive to body chemistry at the implantation site, the reservoir 302 is preferably made of titanium or a titanium alloy having greater than 60%, often greater than 85% titanium.

The diameter of the flow modulator 200 may be selected such that the flow modulator 200 can be press-fitted into the open end 304 of the reservoir 302. It is also possible to include features such as threads on the outer surface 220 of the outer shell 202 and the inner surface 310 of the reservoir 302 for securing the flow modulator 200 to the reservoir 302.

The following examples are illustrative of the invention and are not to be construed as limiting the invention as otherwise described herein.

An osmotic delivery system, as illustrated in FIG. 3, containing interferon-omega (IFN-ω) for the treatment of, for example, hepatitis C was assembled from the following components: (i) reservoir made of implant grade titanium alloy and having undercuts at an end thereof, (ii) osmotic engine including two cylindrical tablets, each tablet including primarily sodium chloride salt with cellulosic and povidone binders, (iii) piston, (iv) semipermeable plug made of polyurethane and having retaining ribs that mate with undercuts in reservoir, (v) flow modulator having a spiral internal flow channel with a D-shaped cross-section, a diameter of 0.25 mm, and a spiral length of 35 mm, and (vi) a suspension formulation including a particle formulation of IFN-ω suspended in a non-aqueous vehicle.

Figure 4:
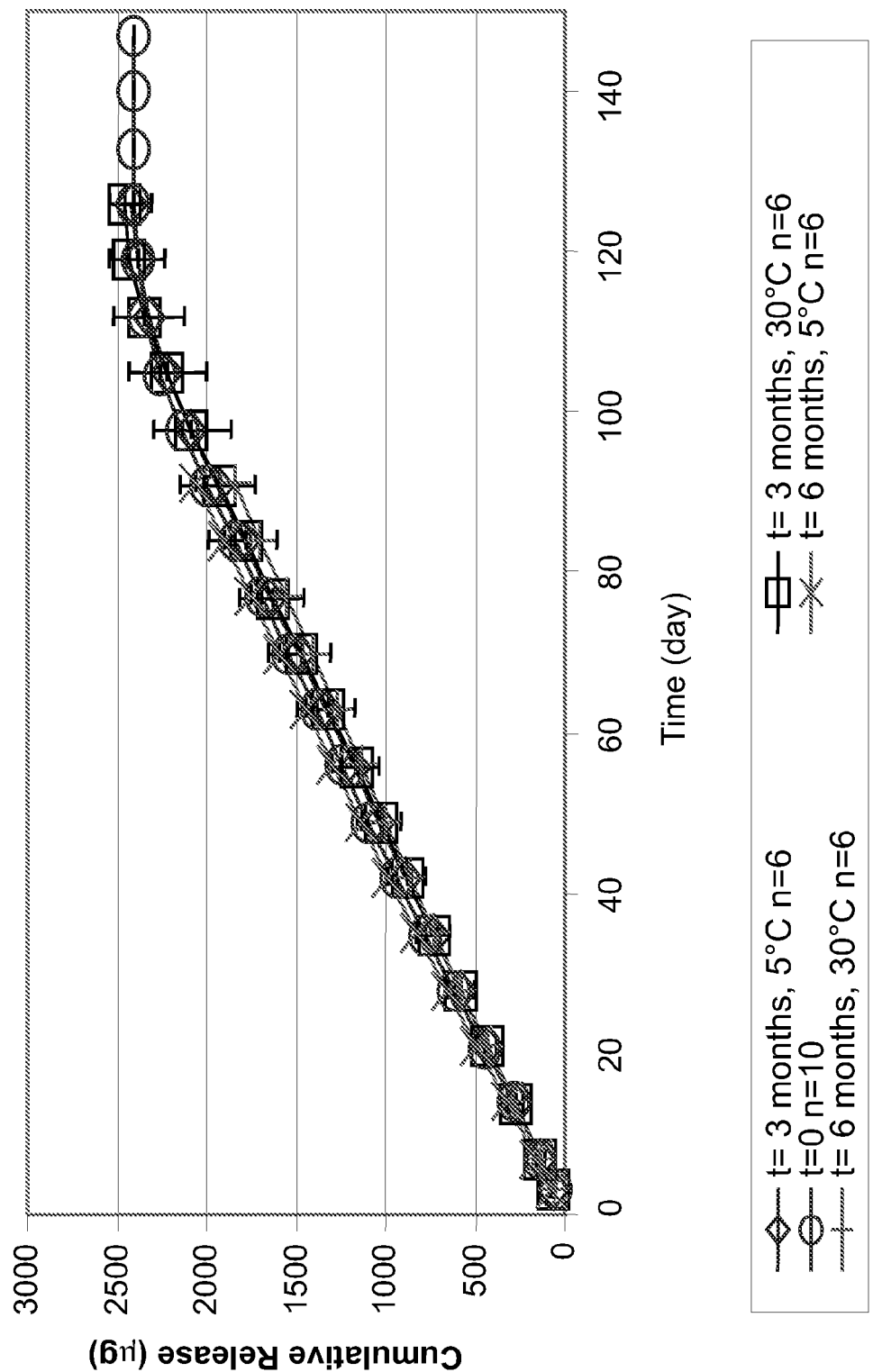
FIG. 4 depicts an in vitro cumulative release of an active agent using an osmotic delivery system according to FIG. 3.

Reservoirs of several osmotic delivery systems, as described above, were filled with 150-μL of the suspension formulation. The semipermeable plug ends of the osmotic delivery systems were placed into glass vials filled with phosphate buffer solution (PBS), and the flow modulator ends of the osmotic delivery systems were placed into glass vials filled with an aqueous release media. The systems were stored or incubated at 5° C. or 30° C., respectively. At specified time points, the release media was removed and exchanged for fresh solution. The sampled release media was analyzed for active agent content using Reversed Phase High Performance Liquid Chromatography (RP-HPLC). FIG. 4 shows in vitro cumulative release of IFN-ω over 6 months.

The invention may provide the following advantages. The two-piece flow modulator enables flexibility in design and manufacturability of the flow modulator. The outer shell is not integral with the reservoir and enables the channel in the flow modulator to be inspected prior to insertion of the flow modulator in the reservoir. The two-piece flow modulator minimizes additional mechanical forces on the channel during insertion of the flow modulator in the reservoir. The two-piece flow modulator enables flexibility to optimize the dimensions of the fluid channel by changing the channel on the inner core or flow insert while maintaining a common outer sleeve.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An implantable delivery system for an active agent formulation, comprising:
a reservoir made of an impermeable material;
a first chamber in the reservoir containing an osmotic engine;
a second chamber in the reservoir containing an active agent formulation;
a partition within the reservoir, the partition defining within the reservoir the first chamber containing the osmotic engine and the second chamber containing the active agent formulation;
a semipermeable plug disposed at a first end of the reservoir adjacent the first chamber; and
a flow modulator comprising (i) two pieces, an outer shell and an inner core, and (ii) an internal fluid channel, the flow modulator disposed at a second end of the reservoir adjacent the second chamber, the flow modulator comprising
the outer shell positioned in an opening at the second end of the reservoir, the outer shell comprising an inner surface,
the inner core inserted in the outer shell, the inner core comprising an outer surface, and
the internal fluid channel having a spiral shape defined between the outer shell and the inner core.

2. The implantable delivery system of claim 1, wherein the fluid channel is formed on the outer surface of the inner core which mates with the inner surface of the outer shell.

3. The implantable delivery system of claim 1, wherein the fluid channel is formed on the inner surface of the outer shell which mates with the outer surface of the inner core.

4. The implantable delivery system of claim 1, further comprising a flow insert disposed between the outer shell and inner core, wherein the fluid channel is formed in the flow insert.

5. The implantable delivery system of claim 4, wherein the outer shell, inner core, and flow insert are made of an inert material.

6. The implantable delivery system of claim 5, wherein the inert material is a non-metallic material.

7. The implantable delivery system of claim 1, wherein the outer shell and inner core are made of an inert material.

8. The implantable delivery system of claim 7, wherein the inert material is a non-metallic material.

9. The implantable delivery system of claim 8, wherein the material is polyetheretherketone, polyaryletheretherketone, ultra-high molecular weight polyethylene, fluorinated ethylene-propylene, polymethylpentene, or liquid crystal polymers.

10. The implantable delivery system of claim 1, wherein the outer shell sealingly engages the inner core.

11. The implantable delivery system of claim 1, wherein the inner core includes an outer shoulder and the outer shell includes an inner shoulder, wherein the outer shoulder and inner shoulder engage to prevent expulsion of the inner core from the outer shell.

12. The implantable delivery system of claim 1, wherein a length of the fluid channel ranges from 10 to 50 mm.

13. The implantable delivery system of claim 1, wherein an effective cross-sectional diameter of the fluid channel ranges from 0.1 to 0.5 mm.

14. The implantable delivery system of claim 1, wherein the active agent formulation comprises interferon-omega.

15. The implantable delivery system of claim 1, wherein the flow modulator is press-fitted into the opening at the second end of the reservoir.

16. The implantable delivery system of claim 1, wherein the reservoir comprises titanium or a titanium alloy.

17. The implantable delivery system of claim 1, wherein the partition comprises a slidable piston.

* * * * *

UNITED STATES PATENT AND TRADEMARK OFFICE
CERTIFICATE OF CORRECTION

PATENT NO. : 8,052,996 B2
APPLICATION NO. : 11/755494
DATED : November 8, 2011
INVENTOR(S) : Scott D. Lautenbach et al.

Page 1 of 1

It is certified that error appears in the above-identified patent and that said Letters Patent is hereby corrected as shown below:

Column 5, line 63, delete "$Q_{wd}(res)=C_oQe^{(-QL/D_w A)}$", insert --$Q_{wd}(res) = C_O Qe^{(-QL/D_w A)}$--.

Column 6, line 3, delete "cm .", insert --$cm^2$.--.

Signed and Sealed this
Tenth Day of July, 2012

David J. Kappos
*Director of the United States Patent and Trademark Office*